United States Patent [19]
Williams

[11] Patent Number: 4,898,945
[45] Date of Patent: Feb. 6, 1990

[54] PROCESS FOR 6,7-DIHYDRO-5,8-DIMETHYL-9-FLUORO-1-OXO-1H,5H-BENZO[I,J]QUINOLIZINE-2-CARBOXYLIC ACID

[75] Inventor: Bruce E. Williams, St. Paul, Minn.

[73] Assignee: Minnesota Mining and Manufacturing Company, St. Paul, Minn.

[21] Appl. No.: 268,608

[22] Filed: Nov. 4, 1988

Related U.S. Application Data

[63] Continuation of Ser. No. 821,048, Jan. 11, 1986, abandoned.

[51] Int. Cl.$^4$ .................. C07D 455/06; C07D 215/12
[52] U.S. Cl. ...................................... 546/95; 546/166; 546/180
[58] Field of Search ..................... 546/95, 166, 180

[56] References Cited

U.S. PATENT DOCUMENTS

| | | | |
|---|---|---|---|
| 4,301,289 | 11/1981 | Leir et al. | 546/94 |
| 4,380,543 | 4/1983 | Stern | 546/166 |
| 4,443,447 | 4/1984 | Gerster et al. | 546/166 |
| 4,472,405 | 9/1984 | Stern | 424/258 |
| 4,472,407 | 9/1984 | Stern | 546/94 |
| 4,524,148 | 6/1985 | Stern | 546/166 |
| 4,538,003 | 8/1985 | Tam | 568/656 |

OTHER PUBLICATIONS

March J. Adv. Org. Chem. pp. 410–412, 2nd Ed. (1977).
Morrison et al. Org. Chem. pp. 386–387, 3rd Ed (1972).
Kohei Tamao et al., Bulletin Chemical Society of Japan, 49, 1958–1969 (1976).
Bergstrom, et al., Tetrahedron Letters, 23, 4191–4194 (1982).

*Primary Examiner*—Mary C. Lee
*Assistant Examiner*—J. Richter
*Attorney, Agent, or Firm*—Donald M. Sell; Walter N. Kirn; Robert W. Sprague

[57] ABSTRACT

A process for preparing 6,7-dihydro-9-fluoro-5,8-dimethyl-1-oxo-1H,5H-benzo[i,j]quinolizine-2-carboxylic acid, an antimicrobial, using 6-fluoro-2-methylquinoline as a starting material. A synthetic intermediate is also disclosed.

7 Claims, No Drawings

PROCESS FOR 6,7-DIHYDRO-5,8-DIMETHYL-9-FLUORO-1-OXO-1H,5H-BENZO[I,J]QUINOLIZINE-2-CARBOXYLIC ACID

This is a continuation of application Ser. No. 821,048 filed Jan. 11, 1986 abandoned.

This invention relates to the synthesis of benzo[i,j]quinolizines substituted at the 8-position by a methyl group. More specifically it relates to a synthetic process for 6,7-dihydro-5,8-dimethyl-9-fluoro-1-oxo-1H,5H-benzo[i,j]quinolizine-2-carboxylic acid. This invention further relates to certain individual steps of the process and to a novel synthetic intermediate prepared by one such step.

U.S. Pat. No. 4,472,405 describes the synthesis of 6,7-dihydro-5,8-dimethyl-9-fluoro-1-oxo-1H,5H-benzo[i,j]quinolizine-2-carboxylic acid. The synthetic procedure disclosed in that patent utilizes 5-amino-2-fluorobenzoic acid as a starting material to provide 6-fluoro-5-methyl-1,2,3,4-tetrahydroquinaldine and requires two reduction reactions to obtain the intermediate 6-fluoro-5-methyl-1,2,3,4-tetrahydroquinaldine from 6-fluoro-5-carboxyquinaldine. These reduction reactions result in a reduced yield overall, and thus an alternate, more efficient synthesis was desired. The process of Example 1 of the invention provides a higher yield of 6,7-dihydro-5,8-dimethyl-9-fluoro-1-oxo-1H,5H-benzo[i,j]quinolizine-2-carboxylic acid than the process described in U.S. Pat. No. 4,472,405.

U.S. Pat. No. 4,301,289 describes the compounds 6-fluoro-2-methylquinoline, 6-fluoro-2-methyl-1,2,3,4-tetrahydroquinoline, and dialkyl 2-[N-(6-fluoro-2-methyl-1,2,3,4-tetrahydroquinolinyl)]methylenemalonates. U.S. Pat. No. 4,472,407 describes the compound 5-bromo-6-fluoro-2-methylquinoline and its synthesis.

Kohei Tamao et al., Bulletin Chemical Society of Japan, 49, 1958–1969 (1976), describes nickel-catalyzed Grignard displacements of certain aromatic halides. Dichloro[1,3-bis(diphenylphosphino)propane] nickel (II) catalyst is specifically disclosed. Bergstrom et al., Tetrehedron Letters, 23, 4191–4194 (1982), discloses the synthesis of 6-alkyl and 6-aryl substituted 9-β-D-ribofuranosyl purines via the nickel catalyzed coupling of Grignard reagents to 2′,3′,5′-tris-O-(t-butyldimethylsilyl)-9-β-D-ribofuranosyl-6-chloropurine. Dichloro[(1,3-bis(diphenylphosphino)propane] nickel (II) catalyst is again specifically disclosed.

The present invention provides a process for the preparation of 6,7-dihydro-5,8-dimethyl-9-fluoro-1-oxo-1H,5H-benzo[i,j]quinolizine-2-carboxylic acid of Formula I:

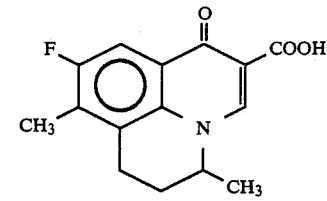

the process comprising:
(1) reacting 6-fluoro-2-methylquinoline (II) with bromine in the presence of a strong Lewis acid to provide 5-bromo-6-fluoro-2-methylquinoline (III):
(2) reacting the quinoline of formula III with a methyl Grignard in the presence of dichloro[1,3-bis(diphenylphosphino)propane] nickel (II) to provide 2,5-dimethyl-6-fluoroquinoline (IV);
(3) reducing the compound of Formula IV in the presence of a catalyst to provide 2,5-dimethyl-6-fluoro-1,2,3,4-tetrahydroquinoline (V);
(4) condensing the tetrahydroquinoline of Formula V with a diester of an alkoxymethylenemalonic acid of Formula VA (wherein "alk" is an alkyl group containing 1 to about 4 carbon atoms and each R′ is independently an alkyl group containing 1 to about 4 carbon atoms or the R's together form an isopropyl radical) to provide a diester of (2,5-dimethyl-6-fluoro-1,2,3,4-tetrahydro-1-quinolinyl)methylenemalonic acid (VI);
(5) cyclizing the compound of Formula VI to provide the ester of 6,7-dihydro-5,8-dimethyl-9-fluoro-1-oxo-1H,5H-benzo[i,j]quinolizine-2-carboxylic acid (VII), and
(6) hydrolyzing the compound of Formula VII to give 6,7-dihydro-5,8-dimethyl-9-fluoro-1-oxo-1H,5H-benzo[i,j]quinolizine-2-carboxylic acid (I).

This invention also relates to processes comprising the reaction of step (2) and, optionally, the reaction of step (3) above.

This invention further relates to the novel intermediate 2,5-dimethyl-6-fluoroquinoline, the product of step (2) above.

More particularly, in one embodiment, the process of the invention is illustrated in the Reaction Scheme below, wherein alk and R′ are as defined above:

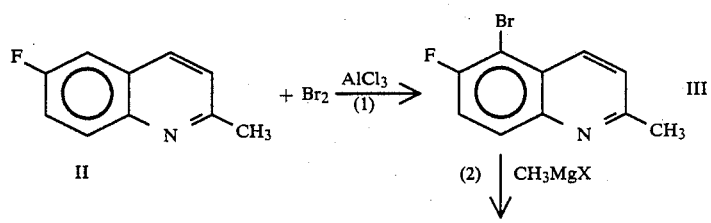

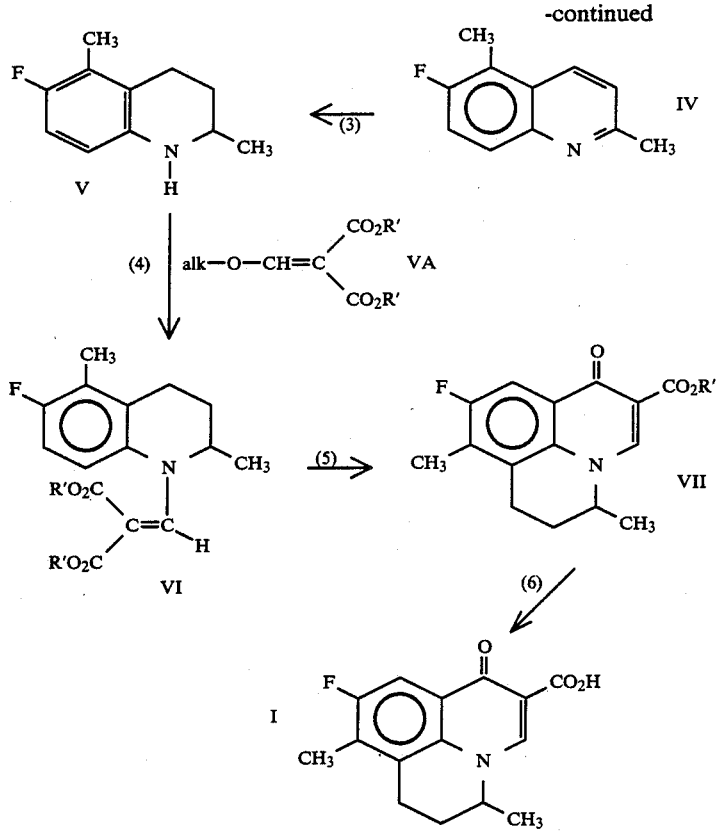

In the first step of the Reaction Scheme the known compound 6-fluoro-2-methylquinoline (II) is reacted with bromine in the presence of a strong Lewis acid such as aluminum chloride at an elevated temperature such as 50°–80° C. The Lewis acid is preferably employed in a ratio of about 1.5 equivalent of the Lewis acid per mole of the quinoline. The reaction may be run neat or in a suitable inert solvent such as 1,2-dichloroethane, chloroform or methylene chloride. It is presently preferred to use a slight, for example, 10%, excess of bromine, but an equimolar amount may also be used if desired. When the reaction is complete, the product may be isolated as a zinc complex which is then freed by addition of a strong base such as ammonium hydroxide. The product of step (1) is 5-bromo-6-fluoroquinaldine (Formula III), a known compound.

Step (2) of the Reaction Scheme requires reacting the 5-bromo-6-fluoroquinaldine (Formula III) with a methyl Grignard reagent in the presence of dichloro[1,3-bis(diphenylphosphino)propane] nickel (II) catalyst. The reaction is run in a solvent such as diethyl ether or toluene at a temperature preferably between 5° C. and 20° C. The Grignard counterion may be bromide or chloride, but chloride is presently preferred. Also, 1.2 to 1.4 equivalents of Grignard may be used, and the nickel catalyst is used in a range of 0.01 to 0.10 equivalents with 0.05 being preferred. The progress of the reaction may be monitored by gas chromatography. When the reaction is complete, the product, which is novel 2,5-dimethyl-6-fluoroquinoline, is extracted into dilute acid, for example, dilute hydrochloric acid and is then precipitated by addition of a base, for example, ammonium hydroxide.

In step (3), the quinoline of Formula IV is reduced to the tetrahydroquinoline of Formula V. The catalysts for this reaction are platinum-based, for example platinum on charcoal, about 0.3 g to 1.0 g of catalyst per 20 g of quinoline being used. The compound of Formula IV is dissolved either in a weak organic acid such as acetic, or in a mixture of a lower alkanol (i.e., one containing one to five carbon atoms) such as isopropanol and a weak organic acid. The mixture is hydrogenated at a pressure of 30 to 60 psi at a temperature of preferably about 20° C. After completion of the reduction reaction the catalyst is removed by filtration and the solvent is evaporated. The residual solid is taken up in an organic solvent such as toluene or 1,2-dichloroethane. The organic solution is washed with base, dried and evaporated to give the product of Formula V.

The 2,5-dimethyl-6-fluoro-1,2,3,4-tetrahydroquinoline of Formula V is condensed with a diester of an alkoxymethylenemalonic acid (VA) in step (4). The preferred diester of Formula VA is diethyl ethoxymethylenemalonate since it is most readily available. Other suitable diesters of alkoxymethylenemalonic acid include cycloisopropylidenyl alkoxymalonates of the formula

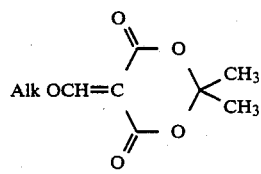

wherein alk is as defined above.

The condensation reaction requires heating the reactants until the reaction is complete as determined by gas chromatography. The reaction is conducted in the absence of solvent at a temperature of 100°–200° C. and preferably 140°–160° C. The alcohol by-product is preferably removed by distillation to drive the reaction to completion. The product of this reaction is the compound of Formula VI. It may be isolated or may be used directly in step (5) without isolation.

In step (5) the intermediate of Formula VI is cyclized to form the intermediate ester of Formula VII. The cyclization step is preferably carried out by heating the intermediate of Formula VI in the presence of phosphorus oxychloride. The reaction may be carried out neat or in a suitable solvent such as toluene. Excess phosphorus oxychloride is destroyed by the addition of either base or ethanol. Alternatively, the cyclization reaction may be carried out by heating the intermediate of Formula VI in the presence of polyphosphoric acid. The isolated product may be used directly in step (6), or it may be purified by recrystallization before using it in step (6).

The ester of Formula VII is saponified in step (6) by conventional means such as hydrolysis in hydrochloric acid to provide 6,7-dihydro-5,8-dimethyl-9-fluoro-1-oxo-1H,5H-benzo[i,j]quinolizine-2-carboxylic acid of Formula I.

Step (6) need not be conducted if step (5) is conducted using polyphosphoric acid since the ester would then be saponified in step (5).

The following examples are provided to illustrate the invention and are not intended to be limiting of the invention. All amounts expressed are by weight unless otherwise indicated.

EXAMPLE 1

Part A. Preparation of 5-Bromo-6-fluoro-2-methylquinoline

A solution of 20.13 g (0.125 mole) of 6-fluoro-2-methylquinoline in 25 ml of 1,2-dichloroethane was added slowly to a mixture of 25.3 g (0.189 mole) of aluminum chloride and 25 ml of 1,2-dichloroethane. The resulting solution was heated to 70° C.–80° C., and 19.98 g (0.125 mole) of bromine was added dropwise thereto. The reaction mixture was heated at 80° C.–85° C. for about 16 hours and was poured onto ice and acidified by adding 100 ml concentrated hydrochloric acid. 17.04 g (0.125 mole) of zinc chloride was added, and the resulting suspension was heated on a steam bath for 15 minutes. After cooling in an ice bath, the complex was collected by filtration and washed sequentially with 100 ml of cold 3N hydrochloric acid and 100 ml of methylene chloride. The complex was slurried in 100 ml of water, and the pH was adjusted to pH 11 with ammonium hydroxide. The product was collected by filtration, washed with water and dissolved in 150 ml of toluene. The toluene solution was treated with magnesium sulfate and decolorizing charcoal, and was then evaporated to give 22.5 g (0.094 mole) of 5-bromo-6-fluoro-2-methylquinoline, a known compound. The structural assignment was confirmed by nuclear magnetic resonance spectral analysis.

Part B. Synthesis of 2,5-Dimethyl-6-fluoroquinoline

Under a nitrogen atmosphere, 28.0 g (0.05 mole) of dichloro[1,3-bis(diphenylphosphino)propane] nickel (II) catalyst (prepared by the method of G. R. Van Hecke and W. DeW. Horrocks, Inorganic Chemistry, 5, 1968 (1966), incorporated herein by reference) was added to a solution of 240 g (1.0 mole) of 5-bromo-6-fluoro-2-methylquinoline in 3.8 liters of toluene. 440 ml (1.4 mole) of 3.17 molar methylmagnesium chloride in tetrahydrofuran was added rapidly to the above mixture, the resulting exotherm being controlled with an ice bath. The reaction was allowed to stir at room temperature overnight. The reaction was treated with 1 liter of water to destroy the excess Grignard reagent, and the organic layer and aqueous layers were then separated. The organic layer was extracted twice with 1 liter portions of 3N hydrochloric acid. The acid extracts were combined, extracted twice with 1 liter portions of methylene chloride, and made basic (pH>9) with ammonium hydroxide and ice. The product was collected as a tan solid (156.4 g, 0.894 mole). This material was recrystallized from 1 liter of hexane to give 77.1 g (0.44 mole) of 2,5-dimethyl-6-fluoroquinoline which was 98.7% pure as determined by gas chromatography analysis.

Part C. Preparation of 2,5-Dimethyl-6-fluoro-1,2,3,4-tetrahydroquinoline 7.0 kg of 2,5-dimethyl-6-fluoroquinoline, 51.5 kg of glacial acetic acid and 350 g of 50% water-wet 5% platinum on carbon catalyst were combined and hydrogenated at 50 psi for 20 hours. Gas chromatography showed residual starting material so an additional 35 g of catalyst was added and the hydrogenation was continued for an additional 2 hours. The mixture was filtered to remove the catalyst and the solvent was then evaporated. The residue was dissolved in 10 gallons of cold water, and the resulting mixture was made basic with ammonium hydroxide to pH 11 while maintaining the temperature below 30° C. The resulting mixture was extracted with 8 gallons of 1,2-dichloroethane and the extract was dried through azeotropic distillation. The dried extract was treated with magnesium sulfate and filtered, and the filtrate was concentrated in vacuo to give a dark oil, 2,5-dimethyl-6-fluoro-1,2,3,4-tetrahydroquinoline, which was used directly in the next step.

Part D. Preparation of Diethyl (2,5-dimethyl-6-fluoro-1,2,3,4-tetrahydro-1-quinolinyl)-methylenemalonate 3350 g (18.7 mole) of 2,5-dimethyl-6-fluoro-1,2,3,4-tetrahydroquinoline and 4445.7 g (20.6 mole) of diethyl ethoxymethylenemalonate were combined and heated to 110° C. The ethanol was removed by atmospheric distillation initially and then through vacuum distillation when the reaction temperature reached 150° C. The resulting material, diethyl (2,5-dimethyl-6-fluoro-1,2,3,4-tetrahydro-1-quinolinyl)methylenemalonate, was used directly in the next step.

Part E. Preparation of Ethyl 6,7-Dihydro-5,8-dimethyl-9-fluoro-1-oxo-1H,5H-benzo[i,j]quinolizine-2-carboxylate A solution of 36.6 mole of diethyl (2,5-dimethyl-6-fluoro-1,2,3,4-tetrahydro-1-quinolinyl)methylenemalonate in 8.0 kg of toluene was added over a period of two hours to 40 kg of refluxing phosphorus oxychloride. Reflux was maintained during the addition and for 1.5 hours after the addition had been completed. The reaction was monitored by gas chromatography. The solvent was evaporated under vacuum. The residue was mixed with 50 kg of cold 1,2-dichloroethane, and a solution of 9.5 kg of sodium hydroxide in 45.5 kg of water was added while maintaining the temperature below 35° C. The organic and aqueous phases were separated and the aqueous layer was extracted with 1,2-dichloroethane. The two organic extracts were combined, dried through azeotropic distillation, and concentrated in vacuo to give a dark solid. This solid was dissolved in 38 kg of denatured ethyl alcohol, filtered to remove insoluble salts and cooled to 10° C. The resulting solid was collected, reslurried with 5 gallons of cold ethanol, and collected and dried to give 6892 g of ethyl 6,7-dihydro-5,8-dimethyl-9-fluoro-1-oxo-1H,5H-benzo[i,j]quinolizine-2-carboxylate. A second crop of 1596 kg was obtained by concentrating and cooling the mother liquors.

Part F. Preparation of 6,7-Dihydro-5,8-dimethyl-9-fluoro-1-oxo-1H,5H-benzo[i,j]quinolizine-2-carboxylic Acid 5.80 kg (19.1 mole) of the ethyl ester from Part E was added to 58 kg of 5% aqueous sodium hydroxide. The mixture was heated to 85° C. over a period of one hour and was then maintained at 85° C. for 0.5 hour. The solution was filtered and then added to a mixture of 18 kg of 30% aqueous hydrochloric acid and 5 gallons of crushed ice. The temperature was kept below 10° C. The resulting solid was collected, rinsed with 10 gallons of water, reslurried with 12 gallons of water, recollected and rinsed with 2 gallons of water. The solid was dried under vacuum at 90° C. to give 5010 g of 6,7-dihydro-5,8-dimethyl-9-fluoro-1-oxo-1H,5H-benzo[i,j]quinolizine-2-carboxylic acid.

EXAMPLE 2

Preparation of 5-Bromo-6-fluoro-2-methylquinoline 20.1 g (0.125 mole) of 6-fluoro-2-methylquinoline was added to 25.3 g (0.189 mole) of aluminum chloride at a temperature of 60° C. 19.98 g (0.125 mole) of bromine was added as a gas. The reaction mixture was heated overnight at 80° C. The reaction mixture was then poured onto ice, and 50% aqueous sodium hydroxide was added until the bulk of the solids had dissolved. The mixture was then extracted with toluene. The toluene extract was dried with magnesium sulfate and evaporated under vacuum to give 23 g of 5-bromo-6-fluoro-2-methylquinoline as a light tan solid. The structure was confirmed by nuclear magnetic resonance spectral analysis.

EXAMPLE 3

Preparation of 5-Bromo-6-fluoro-2-methylquinoline

A solution of 12.1 kg (75 mole) of 6-fluoro-2-methylquinoline in 33 liters of 1,2-dichloroethane was chilled to 5° C., and 15.0 kg (113 mole) of aluminum chloride was added thereto in portions over 15 minutes. The mixture was purged with nitrogen and then heated to 75° C. A solution of 13.2 kg (82.6 mole) of bromine in 2 liters of 1,2-dichloroethane was added over a period of 5.5 hours. The reaction was maintained at 75° C. during the addition and for an additional 15 minutes after the addition was completed. The reaction was stirred at 70° C. for 23 hours and was then cooled to 10° C. and slowly added to a mixture of 8 kg of 30% hydrochloric acid, 41 liters of water and 31.75 kg of ice. The mixture warmed to 50° C. during the addition. The mixture was heated in reflux and the 1,2-dichloroethane was removed by azeotropic distillation. The remaining aqueous solution was cooled to 60° C. and 12 kg of 10% hydrochloric acid was added. The solution was treated with Celite ® (available from Johns-Manville Corp.) and filtered. The filtrate was cooled to 25° C. and 18 kg of 30% hydrochloric acid and 10.22 kg of zinc chloride were added. The resulting slurry was chilled to 5° C. and allowed to stir for several days. The solid was collected and then reslurried with 10 gallons of water. The slurry was chilled to 5° C. and 22 kg of chilled ammonium hydroxide was added. The resulting slurry (pH 10-11) was diluted with 25 gallons of water and the solid was collected, rinsed with water and dried in vacuo at 60° C. to give crude 5-bromo-6-fluoro-2-methylquinoline (84.5% pure by gas chromatography analysis). The material was recrystallized from hexane to give 99.2% pure 5-bromo-6-fluoro-2-methylquinoline.

EXAMPLE 4

Preparation of 2,5-Dimethyl-6-fluoroquinoline

Under a nitrogen atmosphere, 24.0 g (0.1 mole) of 5-bromo-6-fluoro-2-methylquinoline, 2.8 g (0.005 mole) of dichloro[1,3-bisdiphenylphosphinopropane] nickel (II) catalyst, and 380 ml of diethyl ether were combined. 44 ml of 3.17M methylmagnesium chloride in tetrahydrofuran was added dropwise at a rapid rate. The reaction was allowed to stir at room temperature overnight. The ether solution was decanted off into 200 ml of 3N hydrochloric acid in an ice bath, accompanied by vigorous stirring. The aqueous and organic layers were then separated. The aqueous layer was extracted with 100 ml of ethyl acetate and cooled in an ice bath, and the pH was adjusted to pH 10 with concentrated ammonium hydroxide. This was extracted twice with 100 ml of portions of ethyl acetate. The extracts were combined and washed with 30 ml of brine, dried over magnesium sulfate, and filtered and evaporated to give 14.9 g of 2,5-dimethyl-6-fluoroquinoline of 94.4% purity as determined by gas chromatography analysis.

What is claimed is:

1. A process for the preparation of 6,7-dihydro-5,8-dimethyl-9-fluoro-1-oxo-1H,5H-benzo[i,j]quinolizine-2-carboxylic acid comprising the steps of:
   (1) reacting bromine with 6-fluoro-2-methylquinoline to give 5-bromo-6-fluoro-2-methylquinoline, and
   (2) reacting 5-bromo-6-fluoro-2-methylquinoline with a methyl Grignard reagent in the presence of dichloro[1,3-bis(diphenylphosphino)propane] nickel (II) to provide 2,5-dimethyl-6-fluoroquinoline, and
   (3) reducing said 2,5-dimethyl-6-fluoroquinoline to provide the corresponding 2,5-dimethyl-6-fluoro-1,2,3,4-tetrahydroquinoline, and
   (4) condensing said 2,5-dimethyl-6-fluoro-1,2,3,4-tetrahydroquinoline with a diester of an alkoxymethylenemalonic acid of the formula

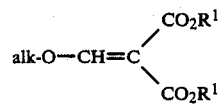

wherein alk is an alkyl group containing 1 to about 4 carbon atoms and each $R^1$ is independently an alkyl group containing 1 to about 4 carbon atoms or the R's together form an isopropyl radical to provide a diester of 2-(N-tetrahydroquinolinyl)methylenemalonic acid, and (5) ring closing said diester of 2-(N-tetrahydroquinolinyl)methylenemalonic acid to provide an ester of 6,7-dihydro-5,8-dimethyl-9-fluoro-1-oxo-1H,5H-benzo[i,j]quinolizine-2-carboxylic acid, and (6) hydrolyzing the ester to give a 6,7-dihydro-5,8-dimethyl-9-fluoro-1-oxo-1H,5H-benzo[i,j]quinolizine-2-carboxylic acid.

2. A process comprising reacting 5-bromo-6-fluoro-2-methylquinoline with a methyl Grignard reagent in the presence of dichloro[1,3-bis(diphenylphosphino)propane] nickel (II) to provide 2,5-dimethyl-6-fluoroquinaldine.

3. A process for the preparation of 2,5-dimethyl-6-fluoro-1,2,3,4-tetrahydroquinoline comprising the steps of:

(1) reacting 5-bromo-6-fluoro-2-methylquinoline with a methyl Grignard reagent in the presence of dichloro[1,3-bis(diphenylphosphino)propane] nickel (II) to provide 2,5-dimethyl-6-fluoroquinoline, and (2) reducing said 2,5-dimethyl-6-fluoroquinoline to provide the corresponding 2,5-dimethyl-6-fluoro-1,2,3,4-tetrahydroquinoline.

4. A process for the preparation of a diester of 2-(N-tetrahydroquinolinyl)methylenemalonic acid comprising the steps of:

(1) reacting 5-bromo-6-fluoro-2-methylquinoline with a methyl Grignard reagent in the presence of dichloro[1,3-bis(diphenylphosphino)propane] nickel (II) to provide 2,5-dimethyl-6-fluoroquinoline, and (2) reducing said 2,5-dimethyl-6-fluoroquinoline to provide the corresponding 2,5-dimethyl-6-fluoro-1,2,3,4-tetrahydroquinoline, and (3) condensing said 2,5-dimethyl-6-fluoro-1,2,3,4-tetrahydroquinoline with a diester of an alkoxymethylenemalonic acid of the formula

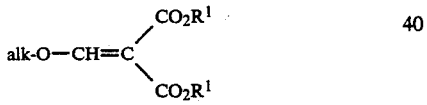

wherein alk is an alkyl group containing 1 to 4 carbon atoms and each $R^1$ is independently an alkyl group containing 1 to about 4 carbon atoms or the two R' moieties together form an isopropyl radical to provide a diester of 2-(N-tetrahydroquinolinyl)methylenemalonic acid.

5. A process for the preparation of an ester of 6,7-dihydro-5,8-dimethyl-9-fluoro-1-oxo-1H,5H-benzo[i,j]quinolizine-2-carboxylic acid comprising the steps of:

(1) reacting 5-bromo-6-fluoro-2-methylquinoline with a methyl Grignard reagent in the presence of dichloro[1,3-bis(diphenylphosphino)propane] nickel (II) to provide 2,5-dimethyl-6-fluoroquinoline, and (2) reducing said 2,5-dimethyl-6-fluoroquinoline to provide the corresponding 2,5-dimethyl-6-fluoro-1,2,3,4-tetrahydroquinoline, and (3) condensing said 2,5-dimethyl-6-fluoro-1,2,3,4-tetrahydroquinoline with a diester of an alkoxymethylenemalonic acid of the formula

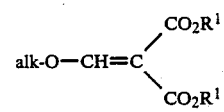

wherein alk is an alkyl group containing 1 to about 4 carbon atoms and each $R^1$ is independently an alkyl group containing 1 to about 4 carbon atoms or the two R' moieties together form an isopropyl radical to provide a diester of 2-(N-tetrahydroquinolinyl)methylenemalonic acid, and (4) ring closing said diester of 2-(N-tetrahydroquinolinyl)methylenemalonic acid to provide an ester of 6,7-dihydro-5,8-dimethyl-9-fluoro-1-oxo-1H,5H-benzo[i,j]quinolizine-2-carboxylic acid.

6. A process for the preparation of 6,7-dihydro-5,8-dimethyl-9-fluoro-1-oxo-1H,5H-benzo[i,j]quinolizine-2-carboxylic acid comprising the steps of:

(1) reacting 5-bromo-6-fluoro-2-methylquinoline with a methyl Grignard reagent in the presence of dichloro[1,3-bis(diphenylphosphino)propane] nickel (II) to provide 2,5-dimethyl-6-fluoroquinoline, and (2) reducing said 2,5-dimethyl-6-fluoroquinoline to provide the corresponding 2,5-dimethyl-6-fluoro-1,2,3,4-tetrahydroquinoline, and (3) condensing said 2,5-dimethyl-6-fluoro-1,2,3,4-tetrahydroquinoline with a diester of an alkoxymethylenemalonic acid of the formula

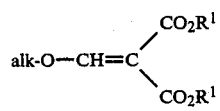

wherein alk is an alkyl group containing 1 to about 4 carbon atoms and each $R^1$ is independently an alkyl group containing 1 to about 4 carbon atoms or the two R' moieties together form an isopropyl radical to provide a diester of 2-(N-tetrahydroquinolinyl)methylenemalonic acid, and (4) ring closing said diester of 2-(N-tetrahydroquinolinyl)methylenemalonic acid to provide an ester of 6,7-dihydro-5,8-dimethyl-9-fluoro-1-oxo-1H,5H-benzo[i,j]quinolizine-2-carboxylic acid, and (5) hydrolyzing the ester to give a 6,7-dihydro-5,8-dimethyl-9-fluoro-1-oxo-1H,5H-benzo[i,j]quinolizine-2-carboxylic acid.

7. 2,5-Dimethyl-6-fluoroquinoline.

* * * * *